United States Patent
Thompson et al.

(10) Patent No.: US 10,522,880 B2
(45) Date of Patent: Dec. 31, 2019

(54) METHOD OF DETECTING METALLIC LITHIUM PRESENT ON AN ELECTRODE

(71) Applicant: GM Global Technology Operations LLC, Detroit, MI (US)

(72) Inventors: Daniel R. Thompson, Liberty, SC (US); John M. Moote, Plymouth, MI (US); Michael P. Balogh, Novi, MI (US); Mark A. Hughes, Jr., Detroit, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 220 days.

(21) Appl. No.: 15/800,608

(22) Filed: Nov. 1, 2017

(65) Prior Publication Data

US 2019/0131669 A1    May 2, 2019

(51) Int. Cl.
| | |
|---|---|
| *H01M 10/48* | (2006.01) |
| *G01N 21/88* | (2006.01) |
| *H01M 2/16* | (2006.01) |
| *H01M 2/34* | (2006.01) |
| *H01M 4/134* | (2010.01) |
| *H01M 10/0525* | (2010.01) |
| *H01M 10/44* | (2006.01) |

(52) U.S. Cl.
CPC ............ *H01M 10/48* (2013.01); *G01N 21/88* (2013.01); *H01M 2/16* (2013.01); *H01M 2/34* (2013.01); *H01M 4/134* (2013.01); *H01M 10/0525* (2013.01); *H01M 10/44* (2013.01)

(58) Field of Classification Search
CPC .... H01M 10/48; H01M 10/0525; H01M 2/16; H01M 2/34; H01M 4/134; G01N 21/33
USPC .......................................................... 429/90
See application file for complete search history.

(56) References Cited

PUBLICATIONS

Mahne, Nika, et al. "Singlet Oxygen Generation as a Major Cause for Parasitic Reactions during Cycling of Aprotic Lithium-Oxygen Batteries." Nature Energy, vol. 2, No. 5, 2017, doi:10.1038/nenergy.2017.36. (Year: 2017).*
Cheng, Xiangyang, et al. "Fluorescence Probing of Active Lithium Distribution in Lithium Metal Anodes." Angewandte Chemie, vol. 131, No. 18, 2019, pp. 5997-6001., doi:10.1002/ange.201900105. (Year: 2019).*
Rochat, Sébastien, and Kay Severin. "Fluorescence Sensors for Lithium Ions and Small Peptides." CHIMIA International Journal for Chemistry, vol. 64, No. 3, 2010, pp. 150-152., doi:10.2533/chimia.2010.150. (Year: 2010).*

* cited by examiner

*Primary Examiner* — Eli S Mekhlin
*Assistant Examiner* — Kourtney R S Carlson
(74) *Attorney, Agent, or Firm* — Quinn IP Law

(57) ABSTRACT

A method of detecting metallic lithium present on an electrode of a lithium ion secondary battery includes depositing a lithium-reactive solution including an oxidized fluorescent dye onto the electrode to form a coated electrode. Concurrent to depositing, the method includes reducing the oxidized fluorescent dye to form a reduced dye and a plurality of lithium ions. The method further includes, after reducing, drying the coated electrode to again form the oxidized fluorescent dye. After drying, the method includes exposing the oxidized fluorescent dye to ultraviolet radiation having a wavelength of from 100 nm to 500 nm to thereby illuminate and detect the metallic lithium. A lithium ion secondary battery system is also disclosed.

13 Claims, 1 Drawing Sheet

METHOD OF DETECTING METALLIC LITHIUM PRESENT ON AN ELECTRODE

INTRODUCTION

The disclosure relates to a lithium ion secondary battery system and to a method of detecting metallic lithium present on an electrode of a lithium ion secondary battery.

Batteries are useful for converting chemical energy into electrical energy, and may be described as primary or secondary. Primary batteries are generally non-rechargeable, whereas secondary batteries are readily rechargeable and may be restored to a full charge after use. As such, secondary batteries may be useful for applications such as powering electronic devices, tools, machinery, and vehicles. For example, secondary batteries for vehicle applications may be recharged external to the vehicle via a plug-in electrical outlet, or onboard the vehicle via a regenerative event.

One type of secondary battery, a lithium ion secondary battery, may include a negative electrode or anode, a positive electrode or cathode, and an electrolyte disposed between the positive and negative electrodes. The negative electrode may be formed from a material that is capable of incorporating and releasing lithium ions during charging and discharging of the lithium ion secondary battery. More specifically, during charging of the battery, lithium ions may move or shuttle from the positive electrode to the negative electrode and embed in the material. Conversely, during battery discharge, lithium ions may be released from the material and move or shuttle from the negative electrode to the positive electrode. During some battery operating conditions, metallic lithium may deposit or plate onto the electrode.

SUMMARY

A method of detecting metallic lithium present on an electrode of a lithium ion secondary battery includes depositing a lithium-reactive solution including an oxidized fluorescent dye onto the electrode to form a coated electrode. Concurrent to depositing, the method includes reducing the oxidized fluorescent dye to form a reduced dye and a plurality of lithium ions. The method further includes, after reducing, drying the coated electrode to again form the oxidized fluorescent dye. After drying, the method includes exposing the oxidized fluorescent dye to ultraviolet electromagnetic radiation having a wavelength of from 100 nm to 500 nm to thereby illuminate and detect the metallic lithium.

In one aspect, depositing may include reacting the lithium-reactive solution with metallic lithium to form the reduced dye. Further, the method may include, after depositing, rinsing the coated electrode with an aprotic solvent to remove an excess unreacted portion of the oxidized fluorescent dye. Rinsing may include repeatedly washing the coated electrode with the aprotic solvent.

In another aspect, drying may include oxidizing the reduced dye to form the oxidized fluorescent dye. Oxidizing may include subjecting the reduced dye to an oxidizing agent selected from the group consisting of hydrogen peroxide and hexafluorophosphate. In a further aspect, oxidizing may include dehydrating the reduced dye in air.

The method may further include, after exposing, creating an optical image of the metallic lithium. In another aspect, the method may include, after exposing, mapping a location of the metallic lithium on the electrode.

In another embodiment, the method includes depositing a lithium-reactive solution including an oxidized fluorescent dye onto the electrode to form a coated electrode. Concurrent to depositing, the method includes reducing the oxidized fluorescent dye to form a reduced dye and a plurality of lithium ions. After reducing, the method includes drying the coated electrode to again form the oxidized fluorescent dye. After drying, the method includes exposing the oxidized fluorescent dye to ultraviolet electromagnetic radiation having a wavelength of from 100 nm to 500 nm to thereby illuminate and detect the metallic lithium. The method also includes, after exposing, rinsing the coated electrode with a fixed quantity of water to remove the oxidized fluorescent dye from the coated electrode and form a rinsate. In addition, the method includes determining a first amount of the oxidized fluorescent dye present in the rinsate and quantifying a second amount of the metallic lithium present on the electrode.

In one aspect, quantifying includes defining a relationship between the first amount and the second amount. In another aspect, quantifying includes correlating the first amount to the second amount.

The method may further include, before rinsing, mapping a location of the metallic lithium on the coated electrode.

A lithium ion secondary battery system includes an electrode of a lithium ion secondary battery. The electrode includes a surface and metallic lithium disposed on the surface. The lithium ion secondary battery system further includes a lithium-reactive solution disposed on the metallic lithium, wherein the lithium-reactive solution includes an oxidized fluorescent dye.

In one aspect, the oxidized fluorescent dye may comprise fluorescein. The fluorescein may be reactive with the metallic lithium and reducible to fluorescin.

In another aspect, the lithium-reactive solution may further include an aprotic solvent. The aprotic solvent may comprise dimethylcarbonate.

The lithium ion secondary battery system may further include a source of ultraviolet electromagnetic radiation having a wavelength of from 100 nm to 500 nm. In one aspect, the metallic lithium is optically detectable on the surface.

The above features and advantages and other features and advantages of the present disclosure are readily apparent from the following detailed description of the best modes for carrying out the disclosure when taken in connection with the accompanying drawings.

DETAILED DESCRIPTION

Figure 1:
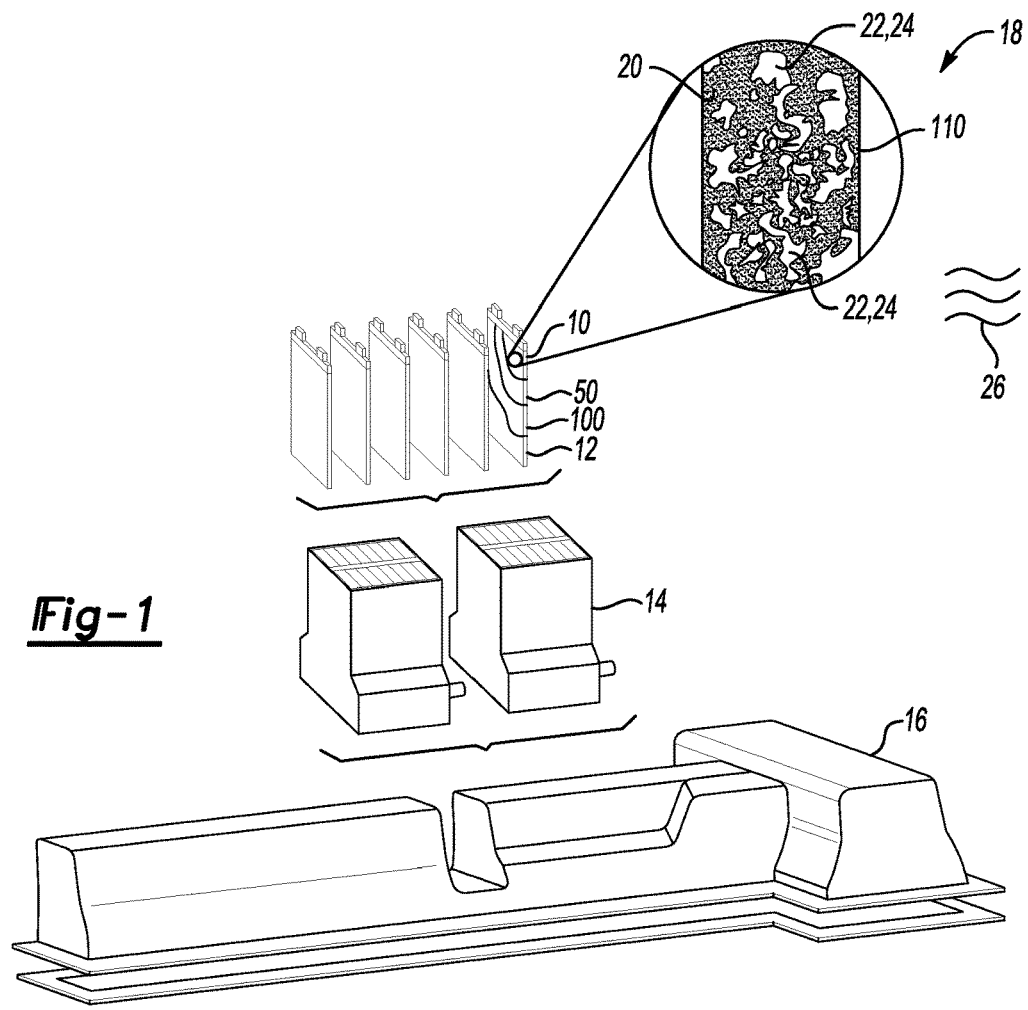
FIG. 1 is a schematic illustration of a perspective view of a lithium ion secondary battery system and includes a magnified view of metallic lithium present on an electrode of a lithium ion secondary battery.

Referring to the Figures, wherein like reference numerals refer to like elements, an electrode 10 of a lithium ion secondary battery 12 is shown generally in FIG. 1. The electrode 10 may be useful for applications requiring lithium ion secondary batteries 12 having excellent electrical conductivity, mechanical integrity, specific energy capacity, performance, and operating life. Therefore, the electrode 10 may be useful for a variety of applications requiring lithium ion secondary batteries 12, such as, but not limited to, electronic devices, tools, machinery, and vehicles. For example, the electrode 10 may be useful for lithium ion secondary batteries 12 for electric and hybrid electric vehicles. However, it is to be appreciated that the electrode 10 may also be useful for non-automotive applications, such as, but not limited to, household and industrial power tools and consumer electronic devices.

Referring again to FIG. 1, a lithium secondary battery module for an automotive application is shown generally at 14. The lithium ion secondary battery module 14 may be useful for automotive applications, such as for a plug-in hybrid electric vehicle (PHEV). Further, a plurality of battery modules 14 may be combined to form a lithium ion secondary battery pack 16, as shown in FIG. 1. By way of example, the lithium ion secondary battery module 14 may be sufficiently sized to provide a required voltage for powering a hybrid electric vehicle (HEV), an electric vehicle (EV), a plug-in hybrid electric vehicle (PHEV), and the like, e.g., approximately 300 to 400 volts or more, depending on the required application.

Further, the lithium ion secondary battery module 14 may include a plurality of lithium ion secondary batteries 12 positioned adjacent to and spaced from one another. Further, each lithium ion secondary battery 12 may have a plurality of electrodes 10, 100, e.g., a positive electrode 100 or cathode and a negative electrode 10 or anode. The electrode 10, 100 described herein may be the positive electrode 100 or the negative electrode 10 of the lithium ion secondary battery 12, depending upon the required configuration and application of the lithium ion secondary battery 12. However, for ease and economy of description, the negative electrode 10 of the lithium ion secondary battery 12 is described below.

The lithium ion secondary battery 12 may be suitable for stacking. That is, the lithium ion secondary battery 12 may be formed from a heat-sealable, flexible foil that is sealed to enclose at least a portion of the electrodes 10, 100 and a separator 50 (FIG. 1). Therefore, a number of lithium ion secondary batteries 12 may be stacked or otherwise placed adjacent to each other to form a cell stack, i.e., the lithium ion secondary battery module 14. Further, although not shown in FIG. 1, additional layers, such as, but not limited to, frames and/or cooling layers may also be positioned in the space between individual lithium ion secondary batteries 12. The actual number of lithium ion secondary batteries 12 may be expected to vary with the required voltage output of each lithium secondary battery module 14. Likewise, the number of interconnected secondary battery modules 14 may vary to produce the required total output voltage for a specific application.

During operation of the lithium ion secondary battery 12, a chemical redox reaction may transfer electrons between a region of relatively negative potential to a region of relatively positive potential to thereby cycle, i.e., charge and discharge, the lithium ion secondary battery 12 and the lithium ion secondary battery pack 16 to provide voltage to power applications. In particular, a plurality of lithium ions may transfer between the positive electrode 100 and negative electrode 10 during charging and discharging of the lithium ion secondary battery 12, as set forth in more detail below.

Referring again to FIG. 1, the electrode 10 of the lithium ion secondary battery 12 may be formed from a substrate. The substrate may be selected according to a desired application of the lithium ion secondary battery 12. As non-limiting examples, the substrate may be formed from aluminum or copper, may be configured as a backing film or foil, and/or may have a thickness of from about 5 microns to about 25 microns, wherein 1 micron is equal to $1 \times 10^{-6}$ meters. For example, for a negative electrode 10, the substrate may be a copper film having a thickness of about 10 microns. For a positive electrode 100, the substrate may be an aluminum film having a thickness of about 20 microns. Further, the substrate may define a plurality of intercalation sites (not shown) into and from which lithium ions may move or shuttle during operation of the lithium ion secondary battery 12.

As shown in FIG. 1, a lithium ion secondary battery system 18 includes the electrode 10, and the electrode 10 includes a surface 20. The electrode 10 further includes metallic lithium 22 disposed on the surface 20. The metallic lithium 22 may be deposited or plated onto the surface 20 during operation of the lithium ion secondary battery 12.

That is, during operation of the lithium ion secondary battery 12, lithium ions may shuttle from the positive electrode 100 to the negative electrode 10. However, during some conditions, the lithium ions may not embed in the substrate if the intercalation sites are filled or nearly filled, such as during conditions involving a comparatively high charge current and/or during comparatively low temperature use. In general, metallic lithium 22 may be disposed on the surface 20 when a transport rate of the lithium ions exceeds a rate at which the lithium ions can be inserted or intercalated into the substrate. For example, during high charge current conditions, the lithium ions may move at a comparatively fast reaction rate and accumulate on the surface 20. Alternatively or additionally, during low temperature use, chemical insertion of lithium ions into the substrate may become too slow and metallic lithium 22 may plate or deposit onto the surface 20.

As described with continued reference to FIG. 1, the lithium ion secondary battery system 18 also includes a lithium-reactive solution 24 disposed on the metallic lithium 22. The lithium-reactive solution 24 may react with the metallic lithium 22 as set forth in more detail below. More specifically, the lithium-reactive solution 24 may be useful for detecting metallic lithium 22 present on the electrode 10 and may serve as a fluorescent tracer for the metallic lithium 22. As such, the lithium-reactive solution 24 may allow an observer to optically detect the metallic lithium 22.

In particular, the lithium-reactive solution 24 includes an oxidized fluorescent dye. The oxidized fluorescent dye may be visible when exposed to a source of ultraviolet electromagnetic radiation (represented generally by 26 in FIG. 1) having a wavelength of from 100 nm to 500 nm, wherein 1 nm is equal to $1 \times 10^{-9}$ meters. As such, the lithium ion secondary battery system 18 may further include the source of ultraviolet electromagnetic radiation 26 such that the metallic lithium 22 may be optically detectable on the surface 20.

Further, the oxidized fluorescent dye may be reducible during a chemical reaction with the metallic lithium 22 disposed on the surface 20 of the electrode 10. The oxidized fluorescent dye may be selected according to a visibility on or contrast with the surface 20. The oxidized fluorescent dye may have a powder form and may be at least slightly soluble in water. In one non-limiting example, the oxidized fluorescent dye may comprise fluorescein and may have a molecular formula of $C_{20}H_{12}O_5$. In another non-limiting example, the oxidized fluorescent dye may comprise fluorescein sodium and may have a molecular formula of $C_{20}H_{10}O_5Na_2$. Further, the oxidized fluorescent dye may be reactive with the metallic lithium 22 and may be reducible to a reduced dye. For example, the fluorescein may be reactive with metallic lithium 22, may be reducible to fluorescin, and may have a molecular formula of $C_{20}H_{14}O_5$.

The lithium-reactive solution 24 may further include an aprotic solvent. Further, the aprotic solvent may have a liquid form and the oxidized fluorescent dye may be soluble in the aprotic solvent to form the lithium-reactive solution 24. In one non-limiting example, the aprotic solvent may comprise dimethylcarbonate and may have a molecular formula of $C_3H_6O_3$.

As set forth in more detail below, the lithium-reactive solution 24 including the oxidized fluorescent dye and the aprotic solvent may react with the metallic lithium 22 such that the oxidized fluorescent dye is reduced to the reduced dye. Conversely, the reduced dye may be oxidized by an oxidizing agent to again form the oxidized fluorescent dye. Further, the oxidized fluorescent dye is fluorescent upon exposure to the source of ultraviolet electromagnetic radiation 26 so that the metallic lithium 22 may be optically detectable.

Figure 2:
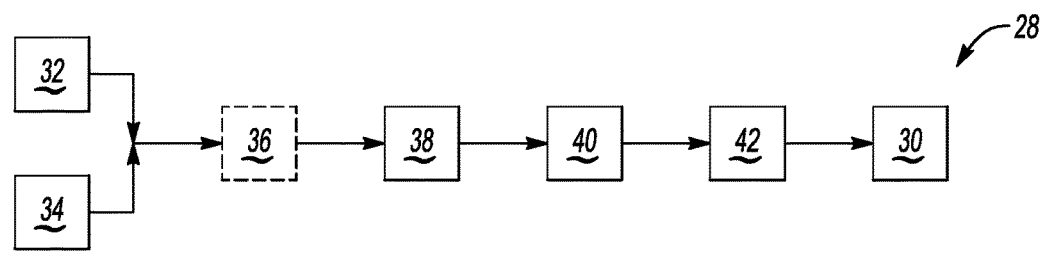
FIG. 2 is a schematic illustration of a method of detecting the metallic lithium present on the electrode of FIG. 1.

More specifically, a method 28 of detecting metallic lithium 22 present on the electrode 10 of the lithium ion secondary battery 12 is shown generally in FIG. 2. The method 28 may be useful for optically detecting metallic lithium 22 plated or deposited on the electrode 10. Further, the method 28 may be useful for pinpointing or mapping 30 a location of the metallic lithium 22 on the electrode 10, i.e., for locating where metallic lithium 22 plating has occurred. In another embodiment illustrated generally in FIG. 3, the method 128 may also be useful for quantifying 46 an amount of metallic lithium 22 deposited on the electrode 10, i.e., for determining how much total metallic lithium 22 has deposited on the electrode 10.

As described with reference to FIG. 2, the method 28 includes depositing 32 the lithium-reactive solution 24 including the oxidized fluorescent dye onto the electrode 10 to form the coated electrode 110. Depositing may include, as non-limiting examples, spraying, blotting, pouring, painting, or coating the oxidized fluorescent dye onto the electrode 10, or may include dipping or immersing the electrode 10 in the oxidized fluorescent dye. For example, the lithium-reactive solution 24 including the oxidized fluorescent dye and the aprotic solvent may be sprayed onto the electrode 10 to thereby coat the metallic lithium 22 present on the electrode 10.

Depositing 32 may further include reacting the lithium-reactive solution 24 with metallic lithium 22 to form the reduced dye. For example, depositing 32 may include reacting a lithium-reactive solution 24 comprising fluorescein and dimethylcarbonate with metallic lithium 22 present on the electrode 10 to form fluorescin, i.e., the reduced dye. Stated differently, the method 28 includes, concurrent to depositing 32, reducing 34 (FIG. 2) the oxidized fluorescent dye to form the reduced dye and a plurality of lithium ions. That is, the solubilized oxidized fluorescent dye may react with the metallic lithium 22 to form a colorless and insoluble reduced dye, lithium ions, and hydroxide ions during a reduction reaction.

Referring again to FIG. 2, the method 28 may further include, after depositing 32, rinsing 36 the coated electrode 110 with the aprotic solvent to remove an excess unreacted portion of the oxidized fluorescent dye. That is, the method 28 may include rinsing 36 the coated electrode 110 with, for example, dimethylcarbonate to remove excess unreacted fluorescein in solution that has not reacted with the metallic lithium 22. More specifically, rinsing 36 may include repeatedly washing the coated electrode, e.g., three or more times, with the aprotic solvent.

Referring again to FIG. 2, the method 28 also includes, after reducing 34, drying 38 the coated electrode 110 to again form the oxidized fluorescent dye. That is, drying 38 may include oxidizing the reduced dye to form the oxidized fluorescent dye. Oxidizing may include subjecting the reduced dye to an oxidizing agent selected from the group consisting of hydrogen peroxide and hexafluorophosphate. The reduced dye may react with the oxidizing agent to again form the oxidized fluorescent dye during an oxidation reaction. Alternatively or additionally, oxidizing may include dehydrating the reduced dye in air.

In addition, the method 28 also includes, after drying 38, exposing 40 the oxidized fluorescent dye to ultraviolet electromagnetic radiation 26 (FIG. 1) having a wavelength of from 100 nm to 500 nm to thereby illuminate and detect the metallic lithium 22. That is, the oxidized fluorescent dye formed during the oxidation reaction described above may illuminate the metallic lithium 22 disposed on the electrode 10 to thereby optically detect the metallic lithium 22. Such metallic lithium 22 may otherwise be difficult or impossible to detect using, for example, nuclear magnetic resonance spectroscopy, x-ray diffraction, differential voltage and differential capacity analysis, and the like. However, in contrast, the oxidized fluorescent dye may absorb the ultraviolet electromagnetic radiation 26 and emit electromagnetic radiation having a comparatively longer wavelength, i.e., exhibit fluorescence, so that an observer can locate the metallic lithium 22 plated on the electrode 10.

Therefore, the method 28 may further include, after exposing 40, creating 42 an optical image of the metallic lithium 22. For example, the method 28 may include photographing the metallic lithium 22 that is illuminated by the oxidized fluorescent dye. The method 28 may also include analyzing one or more optical images of the metallic lithium 22 using image analysis hardware or software. In addition, the method 28 may include, after exposing 40, mapping 30 a location of the metallic lithium 22 on the electrode 10. Therefore, the method 28 may allow an observer to pinpoint or determine a specific area of the electrode 10 in which the metallic lithium plating has occurred.

In another embodiment described with reference to FIG. 3, the method 128 may be useful for determining how much metallic lithium plating has occurred on the electrode 10. Stated differently, in addition to determining where the metallic lithium 22 has deposited onto the electrode 10, the method 128 may also be useful for quantifying 46 how much metallic lithium 22 has deposited onto the electrode 10.

For this embodiment, the method 128 includes, after exposing 40, rinsing 136 the coated electrode 110 with a fixed quantity of water or other solvent to remove the oxidized fluorescent dye and form a rinsate. For example, as set forth above, the method 128 may include, before rinsing 136, mapping 30 the location of the metallic lithium 22 on the coated electrode 110. However, after mapping 30 the location, the method 128 includes rinsing 136 the coated electrode 110 to remove the oxidized fluorescent dye from the coated electrode 110.

Since the coated electrode 110 is rinsed with a fixed or determined quantity of water or other solvent, the method 128 also includes determining 44 a first amount of the oxidized fluorescent dye present in the rinsate. For example, the rinsate may be weighed to determine the first quantity. Alternatively or additionally, a volume of the rinsate may be measured to determine the first quantity.

Figure 3:
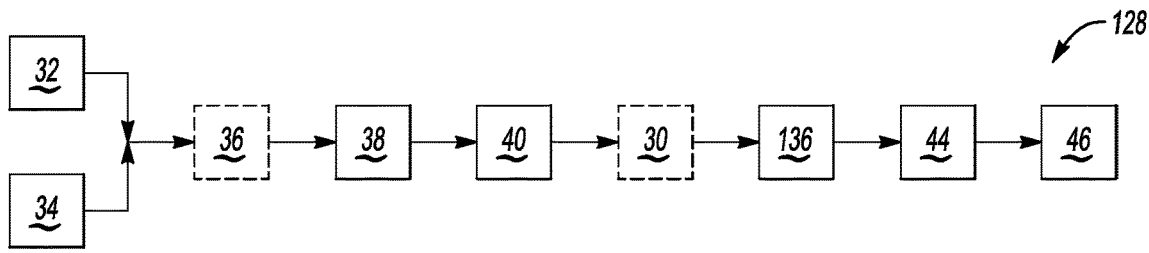
FIG. 3 is a schematic illustration of another embodiment of the method of FIG. 2.

Therefore, as described with continued reference to FIG. 3, the method 128 also includes quantifying 46 a second amount of the metallic lithium 22 present on the electrode 10. That is, quantifying 46 may include correlating the first amount to the second amount, i.e., connecting the first amount of the oxidized fluorescent dye present in the rinsate to the second amount of metallic lithium 22 present on the electrode 10. For example, quantifying 46 may include, but is not limited to, defining a relationship between the first amount and the second amount according to the relationships set forth at (I).

$$S_{Li} = f(m_{FL}) \quad (I)$$

$$S_{Li} = \frac{m_{FL}}{M_{FL}} \cdot W_T$$

wherein $S_{Li}$ is a sum of the total amount of metallic lithium 22;

$m_{FL}$ is a mass of the oxidized fluorescent dye present in the rinsate;

$M_{FL}$ is the molar mass of the oxidized fluorescent dye; and $W_T$ is a ratio based on mols of lithium expected to react with mols of oxidized fluorescent dye.

Advantageously, the method 28, 128 and lithium ion secondary battery system 18 allow for detecting, locating, and quantifying 46 an amount of metallic lithium 22 present on the electrode 10. The oxidized fluorescent dye, after reduction and oxidation as set forth above, serves as an accurate visual tracer or contrast agent to pinpoint a location of the metallic lithium 22. Further, the method 28, 128 is automatable and therefore allows for economical detection and analysis of plated metallic lithium 22 on the electrode 10. Therefore, the method 28, 128 is efficient, cost-effective, and capable of comparatively high run rates with minimal equipment downtime.

While the best modes for carrying out the disclosure have been described in detail, those familiar with the art to which this disclosure relates will recognize various alternative designs and embodiments for practicing the disclosure within the scope of the appended claims.

What is claimed is:

1. A method of detecting metallic lithium present on an electrode of a lithium ion secondary battery, the method comprising:
    depositing a lithium-reactive solution including an oxidized fluorescent dye onto the electrode to form a coated electrode;
    concurrent to depositing, reducing the oxidized fluorescent dye to form a reduced dye and a plurality of lithium ions;
    after reducing, drying the coated electrode to again form the oxidized fluorescent dye; and
    after drying, exposing the oxidized fluorescent dye to ultraviolet electromagnetic radiation having a wavelength of from 100 nm to 500 nm to thereby illuminate and detect the metallic lithium.

2. The method of claim 1, wherein depositing includes reacting the lithium-reactive solution with metallic lithium to form the reduced dye.

3. The method of claim 2, further including, after depositing, rinsing the coated electrode with an aprotic solvent to remove an excess unreacted portion of the oxidized fluorescent dye.

4. The method of claim 3, wherein rinsing includes repeatedly washing the coated electrode with the aprotic solvent.

5. The method of claim 1, wherein drying includes oxidizing the reduced dye to form the oxidized fluorescent dye.

6. The method of claim 5, wherein oxidizing includes subjecting the reduced dye to an oxidizing agent selected from the group consisting of hydrogen peroxide and hexafluorophosphate.

7. The method of claim 5, wherein oxidizing includes dehydrating the reduced dye in air.

8. The method of claim 1, further including, after exposing, creating an optical image of the metallic lithium.

9. The method of claim 1, further including, after exposing, mapping a location of the metallic lithium on the electrode.

10. A method of detecting metallic lithium present on an electrode of a lithium ion secondary battery cell, the method comprising:
    depositing a lithium-reactive solution including an oxidized fluorescent dye onto the electrode to form a coated electrode;
    concurrent to depositing, reducing the oxidized fluorescent dye to form a reduced dye and a plurality of lithium ions;
    after reducing, drying the coated electrode to again form the oxidized fluorescent dye;
    after drying, exposing the oxidized fluorescent dye to ultraviolet electromagnetic radiation having a wavelength of from 100 nm to 500 nm to thereby illuminate and detect the metallic lithium;
    after exposing, rinsing the coated electrode with a fixed quantity of water to remove the oxidized fluorescent dye and form a rinsate;
    determining a first amount of the oxidized fluorescent dye present in the rinsate; and
    quantifying a second amount of the metallic lithium present on the electrode.

11. The method of claim 10, wherein quantifying includes defining a relationship between the first amount and the second amount.

12. The method of claim 11, wherein quantifying includes correlating the first amount to the second amount.

13. The method of claim 10, further including, before rinsing, mapping a location of the metallic lithium on the coated electrode.

* * * * *